US00PP29480P3

(12) United States Plant Patent
Bourne

(10) Patent No.: US PP29,480 P3
(45) Date of Patent: Jul. 10, 2018

(54) ***DIANTHUS* PLANT NAMED 'WP15 MOW08'**

(50) Latin Name: *Dianthus caryophyllus*
Varietal Denomination: WP15 MOW08

(71) Applicant: Plant Genetics International Limited, SouthHavant, Hampshire (GB)

(72) Inventor: Carolyn Grace Bourne, Dawlish (GB)

(73) Assignee: Plant Genetics International Limited, Havant (GB)

( * ) Notice: Subject to any disclaimer, the term of this patent is extended or adjusted under 35 U.S.C. 154(b) by 0 days.

(21) Appl. No.: 15/330,575

(22) Filed: Oct. 13, 2016

(65) Prior Publication Data

US 2017/0118900 P1 Apr. 27, 2017

(30) Foreign Application Priority Data

Oct. 23, 2015 (QZ) ..... PBR 2015/2451

(51) Int. Cl.
*A01H 5/02* (2018.01)

(52) U.S. Cl.
USPC ..... Plt./273

(58) Field of Classification Search
USPC ..... Plt./273, 276, 272
CPC ..... A01H 5/0233; A01H 5/02; A01H 5/00; A01H 5/0227
See application file for complete search history.

(56) References Cited

PUBLICATIONS

FlipSnack Whetman Pinks retrieved on Oct. 2, 2017, retrieved from the Internet at https://www.flipsnack.com/redearth1/whetman-pinks-catalogue-2015.html, one page. (Year: 2017).*

Whetman Pinks Wholesale Review 2015 Catalogue, retrieved onSep. 18, 2017, retrieved from the Internet at http://www.earleyornamentals.co.uk/upload/files/Whetman-Pink-Catalogue.pdf, pp. 1-24 (Year: 2015).*

* cited by examiner

*Primary Examiner* — June Hwu
(74) *Attorney, Agent, or Firm* — James M. Weatherly; Bethany R. Roahrig; Cochran Freund & Young, LLC

(57) ABSTRACT

A new cultivar of *Dianthus* plant named 'WP15 MOW08' that is characterized by a compact mounding habit, double light pink flowers with vivid magenta stripes and speckles, strong, clove-like fragrance, blooming from May through October, with glaucous blue-green foliage, suitable for use as a flowering plant in pots and containers as well as for use as a cut flower, is disclosed.

2 Drawing Sheets

Genus and species: *Dianthus caryophyllus*.
Variety denomination: 'WP15 MOW08'.

CROSS REFERENCE TO RELATED APPLICATIONS

This application claims the benefit of priority under 35 U.S.C. 119 (f) to the application for European Community Plant Variety Rights which was filed for the instant plant variety on Oct. 23, 2015, File Number 2015/2451.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus caryophyllus* and will be referred to hereinafter by the cultivar name 'WP15 MOW08'.

'WP15 MOW08' is a complex hybrid plant that is the product of a long term breeding program conducted in a cultivated area of Houndspool, Dawlish, Devon, United Kingdom. 'WP15 MOW08' was selected in 2008 for its double light pink flowers with vivid magenta stripes and speckles, strong clove-like fragrance and glaucous blue-green foliage.

'WP15 MOW08' arose and was selected as a seedling which resulted from the controlled pollination of two prior seedlings arising and retained from the breeding program. The male parent is *Dianthus* code name 'MOW 02.09' (unpatented) and the female parent is *Dianthus* code name 'Tricia' (unpatented).

Asexual reproduction of 'WP15 MOW08' was first accomplished in 2008 in a cultivated area of Houndspool, United Kingdom using the propagation method of shoot cuttings. 'WP15 MOW08' has been determined to be stable and reproduces true to type in successive generations of asexual propagation.

SUMMARY

The following traits have been repeatedly observed and represent the characteristics of the new *Dianthus* cultivar 'WP15 MOW08'. 'WP15 MOW08' has not been tested under all possible conditions and phenotypic differences may be observed with variations in environmental, climatic and cultural conditions, however, without any variance in genotype.

1. 'WP15 MOW08' exhibits a compact mounding habit.
2. 'WP15 MOW08' bears double light pink flowers with magenta stripes and speckles.
3. The petals of 'WP15 MOW08' are ruffled.

4. 'WP15 MOW08' blooms from May through October.
5. The flowers of 'WP15 MOW08' exhibit a strong, clove-like fragrance.
6. 'WP15 MOW08' exhibits glaucous blue-green foliage.
7. At maturity, the height of the foliage mound of 'WP15 MOW08' is 35 to 40 cm and the width is 20 cm to 25 cm.
8. 'WP15 MOW08' is perennial and hardy at least to minus 15° Centigrade.
9. 'WP15 MOW08' is suitable for use as a flowering plant in pots, containers and as a cut flower.

BRIEF DESCRIPTION OF THE PHOTOGRAPHS

The accompanying color photographs illustrate the overall appearance of the new *Dianthus* variety 'WP15 MOW08' showing colors as true as it is reasonably possible to obtain in colored reproductions of this type. Colors in the photographs may differ from the color values cited in the detailed botanical description, which accurately describe the actual colors of the new variety 'WP15 MOW08'.

Figure 1:
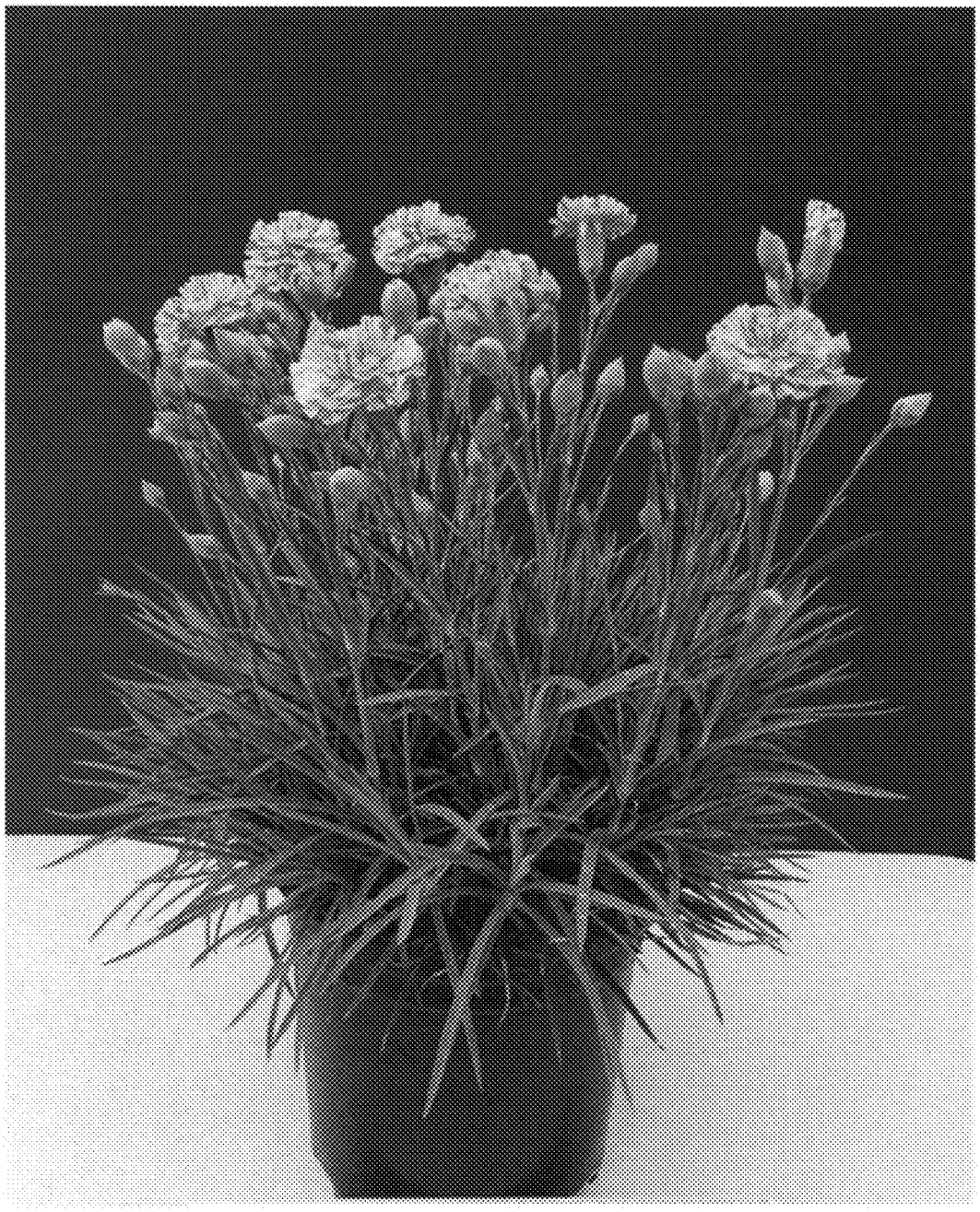
FIG. 1 depicts an entire flowering plant of 'WP15 MOW08'.
Figure 2:
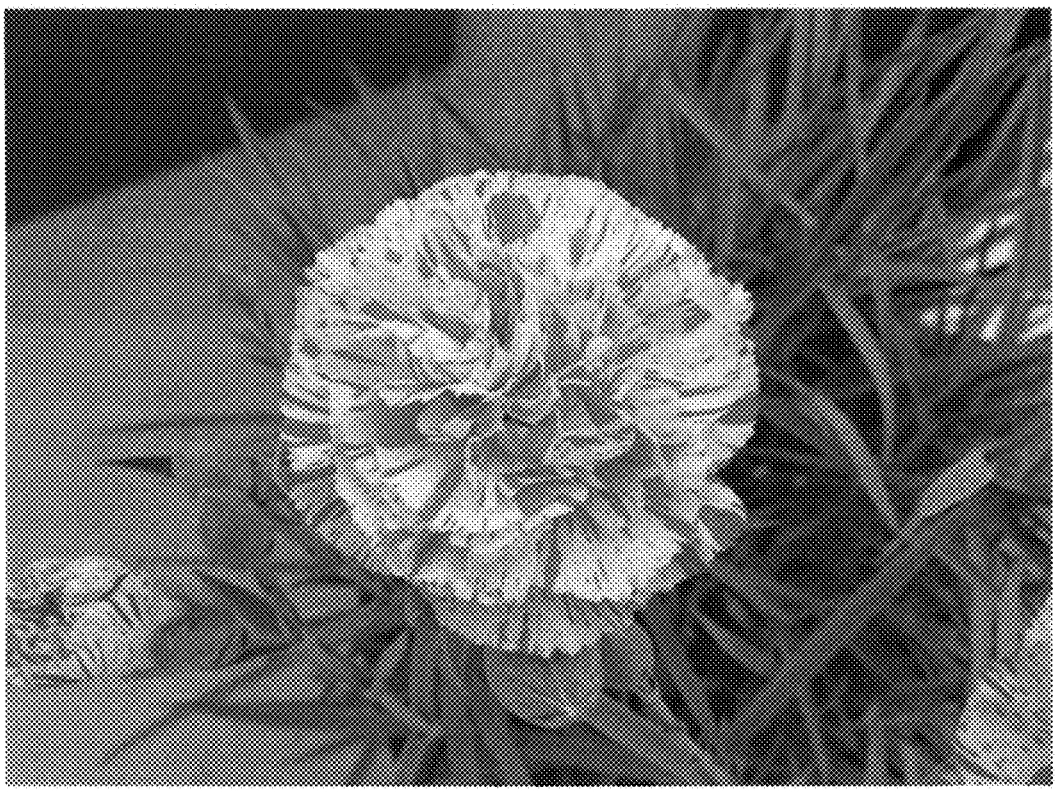
FIG. 2 depicts a close-up view of the flower of 'WP15 MOW08'.

Photographs were taken in August 2015 in Oxnard, Calif. of five-month old plants which have been grown outdoors in 1.5-liter containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP15 MOW08'. Data was collected from plants grown in 3-liter containers under an unheated glasshouse in Houndspool, Dawlish, Devon, United Kingdom. The color determinations are in accordance with the sixth edition (2015) of The Colour Chart of The Royal Horticultural Society, London, England, except where general color terms of ordinary dictionary significance are used. No chemicals were used to treat the plants. Growing conditions are typical for asexually reproduced varieties of hardy *Dianthus*.

Botanical classification: *Dianthus*.

*Variety*.—'WP15 MOW08'.

*Species*.—*Caryophyllus*.

*Common names*.—Hybrid *dianthus*, Garden Pink.

*Commercial classification*.—Hardy perennial.

*Use*.—Ornamental plant for pots and containers.

Parentage: 'WP15 MOW08' is a hybrid plant that resulted from the controlled cross pollination between two *Dianthus* selections as follows: Female parent plant: 'Tricia' experimental *Dianthus* plant (unpatented). Male parent plant: 'MOW 02.09' experimental *Dianthus* plant (unpatented).

Plant description:

*Bloom period*.—May to October.

*Plant habit*.—Compact mounding habit.

*Plant height*.—35 to 40 cm in overall height, including flower canopy.

*Plant width*.—20 cm to 25 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—15 cm in length, 6 mm diameter.

*Surface*.—Glabrous and glaucous.

*Color*.—145B and 145C (in the sheathing zone).

*Branching*.—Numerous shoots from the axils of the lower leaves.

*Internodes* (*fully grown non-flowering shoot*).—8 mm to 10 mm between nodes (before extension of peduncle).

*Node dimensions*.—3 mm in diameter and 4 mm in length.

Leaf:

*Type*.—Evergreen.

*Dimensions*.—12 cm in length, 4 mm in width.

*Color* (*adaxial and abaxial surfaces*).—Ranges between N189B and N189C.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Curvature*.—Weak to none except moderately recurved at base of plant.

*Surfaces* (*adaxial and abaxial*).—Glaucous.

*Fragrance*.—Absent.

Flowers:

*Inflorescence*.—Simple cyme.

*Type*.—Double, polypetalous.

*Position*.—Flowers are held slightly above the foliage.

*Number*.—5 to 7 per stem.

*Dimensions* (*including calyx*).—40 mm to 44 mm in length and 52 mm to 54 mm in diameter.

*Shape*.—Circular.

*Lastingness*.—10 days at 20° Celsius on the plant; 8 to 10 days off the plant.

*Fragrance*.—Strong, clove-like.

*Flowering period*.—May to October.

Peduncle:

*Shape*.—Cylindrical, solid.

*Dimensions*.—25 cm to 30 cm in length, 2 mm to 3 mm in diameter.

*Number of nodes per peduncle*.—5 to 6.

*Surface*.—Glabrous, waxy.

*Strength*.—Strong, rigid.

*Color*.—N189C to N189D.

Bud:

*Shape*.—Obovate (when cracking color).

*Color*.—145B towards base of bud, becoming (ranging between) 137A and 189A towards bud apex.

*Anthocyanin*.—Absent.

*Dimensions*.—25 mm in length and 13 mm in width (described when just cracking color).

Petals:

*Corolla*.—Upper part of corolla convex, lower part of corolla concave.

*Petal arrangement*.—Persistent, apopetalous and overlapping.

*Margin*.—Crenate-dentate.

*Indentations*.—Mainly narrow (0 to 2 mm) but some up to 4 mm deep.

*Texture*.—Soft.

*Type*.—Double.

*Number of petals*.—40 to 50 petals.

*Dimensions*.—43 mm to 45 mm in length, 28 mm to 30 mm in width.

*Petal shape*.—Fan shape.

*Petal surface*.—Glabrous.

*Petal apex*.—Fan shaped, crenate-dentate.

*Petal base*.—Strap shaped, tapering towards base.

*Color pattern*.—Blade is light pink with vivid magenta speckles, stripes and splotches as follows: Numerous (approximately 50-70) speckles distributed throughout every petal. Speckles appear as dots or very short narrow stripes not exceeding 1 mm in width and 3 mm in length. Many (up to 10) stripes appear on each petal ranging from 2 mm in width and 3 mm in length to 4 mm in width and 1 cm in length. Occasional large splotches are present especially in inner petals, approximately 5 mm in width and 1 cm in length.

*Petal color* (*adaxial surface*).—Ground color of blade: 62D. Color of stripes and speckles: N57A and N57B. Color of middle of strap: 145C. Color of base of strap: 145D.

*Petal color* (*abaxial surface*).—Ground color of blade: 62D. Color of stripes and speckles: between 58A and 60D. Color of middle of strap: 145C. Color of base of strap: 145D.

Calyx:

*Dimensions*.—25 mm in length and 12-14 mm in width.

*Shape*.—Cylindrical.

*Sepals*.—5, fused to 8 mm below the apex.

*Sepal dimensions*.—25 mm in length and 10 mm in width.

*Apex*.—Subacute.

*Base*.—Truncate.

*Color of sepals, outer surface*.—137B fading to 137D at the base.

*Color of sepals, inner surface*.—139C fading to 139D at the base.

*Anthocyanin*.—Absent.

*Splitting*.—Not observed.

Epicalyx:

*Number of bracts*.—1 outer pair, 1 inner pair arranged alternately.

*Bract apex shape*.—Acute.

*Bract dimensions*.—12 mm in length and 10 to 13 mm.

*Bract color*.—Ranges between N138A, N138B, N138C and N138D, from apex to base.

*Anthocyanin*.—Absent.

Reproductive organs:

*Stamen number*.—10 to 15 true stamens, plus 5 to 15 petaloid stamens with misshapen anthers have also been observed.

*Stamen dimensions*.—19 mm to 23 mm length and 0.5 mm diameter.

*Color of filaments*.—Whiter than NN155D.

*Anther number*.—10 to 15.

*Anther dimensions*.—4 mm length and 0.5 mm in diameter.

*Color of anthers*.—White, whither than NN155D with slight a pink hue.

*Anther attachment*.—Dorsifixed.

*Pollen*.—Present, dust color closest to N155A.

*Style number*.—Up to 5.

*Style shoulder*.—Absent.

*Color of style*.—Whiter than NN155D.

*Style dimensions*.—30 mm in length and 1 mm in width.

*Stigma number*.—One on each style.

*Stigma color*.—Pink hue, close to 64C.

*Stigma dimensions*.—Up to 5 mm long along the top of the style, fimbriated zone barely visible, slightly above petals at maturity.

*Ovary position*.—Superior.

*Ovary dimensions*.—9 mm in length and 7 mm in diameter.

*Ovary shape*.—Spindle, often deformed.

*Ovary surface and texture*.—Smooth and slightly ribbed.

*Ovary color*.—149B and 149C at the uppermost surface, becoming paler 150D at the lowest surface.

Seed: Seed has not been observed to date.

Diseases and pests: Susceptible to known *Dianthus* pests and disease but no other susceptibilities to pests or disease are known.

COMPARISON WITH PARENTAL LINE AND KNOWN VARIETY

'WP15 MOW08' is distinguishable from the male parent as follows. Whereas the plant shape of 'MOW 02.09' is similar to 'WP15 MOW08', the vegetative habit of the two varieties is very different. 'MOW 02.09' is more vigorous than 'WP15 MOW08' and exhibits a darker green foliage and a looser habit. In addition, the flower color of 'MOW 02.09' is white with a maroon eye.

'WP15 MOW08' is distinguishable from the female parent as follows. Whereas the plant shape of 'Tricia' is similar to 'WP15 MOW08', 'Tricia' has wider, darker grey-green leaves than 'WP15 MOW08'. In addition, the flowers of 'Tricia' are looser, medium pink in color with a darker eye. Neither of the parents exhibit stripes or speckles in their flower pattern.

The variety of *Dianthus* considered to most closely resemble 'WP15 MOW08' is *Dianthus* Plant Named 'Baileys Celebration'. In comparison with 'Baileys Celebration', 'WP15 MOW08' is approximately one-third shorter and bears flowers which are brighter and more perfumed. Whereas the flowers of 'Baileys Celebration' have pink stripes and a brown center, the stripes of 'WP15 MOW08' are darker, more prominent and more regular.

I claim:

1. A new and distinct cultivar of *Dianthus* plant named 'WP15 MOW08' as described and illustrated herein.

* * * * *